US012533116B2

(12) United States Patent
Catania

(10) Patent No.: US 12,533,116 B2
(45) Date of Patent: Jan. 27, 2026

(54) RIB RETRACTOR WITH COMPLIANT RETRACTOR BLADE

(71) Applicant: Edwards Lifesciences Corporation, Irvine, CA (US)

(72) Inventor: Pablo Hernan Catania, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 231 days.

(21) Appl. No.: 18/056,699

(22) Filed: Nov. 17, 2022

(65) Prior Publication Data

US 2023/0078407 A1 Mar. 16, 2023

Related U.S. Application Data

(63) Continuation of application No. PCT/US2021/032509, filed on May 14, 2021.

(60) Provisional application No. 63/026,298, filed on May 18, 2020.

(51) Int. Cl.
*A61B 17/02* (2006.01)
*A61B 17/00* (2006.01)

(52) U.S. Cl.
CPC *A61B 17/0206* (2013.01); *A61B 2017/00407* (2013.01)

(58) Field of Classification Search
CPC .................................................. A61B 17/0206
See application file for complete search history.

(56) References Cited

U.S. PATENT DOCUMENTS 1,810,466 A 6/1931 Deutsch
2,070,670 A 2/1937 Marshall
2,305,289 A 12/1942 Coburg
2,701,562 A 2/1955 Michael et al.
(Continued)

FOREIGN PATENT DOCUMENTS

EP 2572647 A1 * 3/2013 ......... A61B 17/0206
WO 9732514 A2 9/1997
(Continued)

OTHER PUBLICATIONS

English translation of EP 2572647 A1 (2024).*
(Continued)

*Primary Examiner* — Julianna N Harvey
*Assistant Examiner* — Anna V. Little
(74) *Attorney, Agent, or Firm* — Farjami & Farjami, LLP

(57) ABSTRACT

A retractor blade includes a descender portion and a hook portion. The descender portion is configured to engage a rib in response to a retraction force applied to the retractor blade. The hook portion forms a channel with the descender portion. The channel is configured to secure the rib against the descender portion. The descender portion and the hook portion are integrally formed of a compliant material. The first hook portion includes at least one gap separating a plurality of teeth. The at least one gap of the hook portion and the compliant material together are configured to cause substantially an entire length of the retractor blade in the descender portion to conform to the rib in response to the retraction force. The retractor blade may be pivotably attached to an arm of a retractor that is configured to mechanically retract in response to the retraction force.

12 Claims, 8 Drawing Sheets

(56) References Cited

U.S. PATENT DOCUMENTS

| | | | | |
|---|---|---|---|---|
| 2,739,587 A | | 3/1956 | Scholl | |
| 3,111,943 A | | 11/1963 | Orndorff | |
| 3,332,417 A | | 7/1967 | Blanford et al. | |
| 3,347,226 A | | 10/1967 | Harrower | |
| 3,347,227 A | | 10/1967 | Harrower | |
| 3,397,692 A | | 8/1968 | Creager, Jr. et al. | |
| 3,416,520 A | | 12/1968 | Creager, Jr. | |
| 3,473,528 A | | 10/1969 | Mishkin et al. | |
| 3,523,534 A | | 8/1970 | Nolan | |
| 3,638,644 A | | 2/1972 | Reick | |
| 3,641,332 A | | 2/1972 | Reick et al. | |
| 3,729,006 A | * | 4/1973 | Wilder | A61L 31/048 600/210 |
| 3,768,477 A | | 10/1973 | Anders et al. | |
| 3,841,332 A | | 10/1974 | Treacle | |
| 3,863,639 A | | 2/1975 | Kleaveland | |
| 4,155,355 A | | 5/1979 | Yamamoto | |
| 4,188,945 A | | 2/1980 | Wenander | |
| 4,188,975 A | | 2/1980 | Bauer | |
| 4,274,398 A | | 6/1981 | Scott, Jr. | |
| 4,387,706 A | | 6/1983 | Glass | |
| 4,412,532 A | | 11/1983 | Anthony | |
| 4,421,107 A | | 12/1983 | Estes et al. | |
| 4,430,991 A | | 2/1984 | Darnell | |
| 4,434,791 A | | 3/1984 | Darnell | |
| 4,492,229 A | | 1/1985 | Grunwald | |
| RE32,021 E | | 11/1985 | Scott, Jr. | |
| 4,553,537 A | | 11/1985 | Rosenberg | |
| 4,560,832 A | | 12/1985 | Bond et al. | |
| 4,562,832 A | | 1/1986 | Wilder et al. | |
| 4,726,356 A | | 2/1988 | Santilli et al. | |
| 4,777,943 A | | 10/1988 | Chvapil | |
| 4,984,564 A | | 1/1991 | Yuen | |
| 5,005,108 A | | 4/1991 | Pristash et al. | |
| 5,052,374 A | | 10/1991 | Alvarez-Jacinto | |
| 5,054,906 A | | 10/1991 | Lyons, Jr. | |
| 5,159,921 A | | 11/1992 | Hoover | |
| 5,195,505 A | | 3/1993 | Josefsen | |
| 5,213,114 A | | 5/1993 | Bailey, Jr. | |
| 5,231,974 A | | 8/1993 | Giglio et al. | |
| 5,263,922 A | | 11/1993 | Sova et al. | |
| 5,351,680 A | | 10/1994 | Jung | |
| 5,363,841 A | * | 11/1994 | Coker | A61B 17/0206 600/211 |
| 5,365,921 A | * | 11/1994 | Bookwalter | A61B 17/0206 403/150 |
| 5,366,478 A | | 11/1994 | Brinkerhoff et al. | |
| 5,391,156 A | | 2/1995 | Hildwein et al. | |
| 5,441,044 A | | 8/1995 | Tovey et al. | |
| 5,452,733 A | | 9/1995 | Sterman et al. | |
| 5,460,170 A | | 10/1995 | Hammerslag | |
| 5,476,510 A | | 12/1995 | Eberhardt et al. | |
| 5,514,157 A | | 5/1996 | Nicholas et al. | |
| 5,520,610 A | | 5/1996 | Giglio et al. | |
| 5,520,611 A | | 5/1996 | Rao et al. | |
| 5,524,644 A | | 6/1996 | Crook | |
| 5,556,417 A | | 9/1996 | Sher | |
| 5,562,690 A | | 10/1996 | Green et al. | |
| 5,571,215 A | | 11/1996 | Sterman et al. | |
| 5,582,577 A | | 12/1996 | Lund et al. | |
| 5,613,751 A | | 3/1997 | Parker et al. | |
| 5,613,937 A | | 3/1997 | Garrison et al. | |
| 5,618,096 A | | 4/1997 | Parker et al. | |
| 5,649,550 A | | 7/1997 | Crook | |
| 5,656,013 A | | 8/1997 | Yoon | |
| 5,681,341 A | | 10/1997 | Lunsford et al. | |
| 5,785,649 A | | 7/1998 | Fowler, Jr. | |
| 5,810,721 A | | 9/1998 | Mueller et al. | |
| 5,888,247 A | | 3/1999 | Benetti | |
| 5,967,970 A | | 10/1999 | Cowan et al. | |
| 5,984,867 A | * | 11/1999 | Deckman | A61B 17/0206 600/231 |
| 6,048,309 A | | 4/2000 | Flom et al. | |
| 6,142,935 A | | 11/2000 | Flom et al. | |
| 6,165,186 A | * | 12/2000 | Fogarty | A61B 17/122 606/157 |
| 6,176,824 B1 | | 1/2001 | Davis | |
| 6,190,311 B1 | | 2/2001 | Glines et al. | |
| 6,193,652 B1 | | 2/2001 | Berky et al. | |
| 6,241,658 B1 | | 6/2001 | Goodrich | |
| 6,254,534 B1 | | 7/2001 | Butler et al. | |
| 6,309,349 B1 | * | 10/2001 | Bertolero | A61B 1/313 600/210 |
| 6,322,500 B1 | * | 11/2001 | Sikora | A61B 17/0206 600/234 |
| 6,451,054 B1 | | 9/2002 | Stevens | |
| 6,478,728 B1 | | 11/2002 | Wright | |
| 6,613,952 B2 | | 9/2003 | Rambo | |
| 6,723,044 B2 | | 4/2004 | Pulford et al. | |
| 6,814,700 B1 | | 11/2004 | Mueller et al. | |
| 7,008,377 B2 | | 3/2006 | Beane et al. | |
| 7,758,500 B2 | | 7/2010 | Boyd et al. | |
| 8,348,998 B2 | | 1/2013 | Pintor et al. | |
| 2003/0060685 A1 | | 3/2003 | Houser et al. | |
| 2003/0095781 A1 | | 5/2003 | Williams | |
| 2003/0149341 A1 | * | 8/2003 | Clifton | A61B 17/0206 600/210 |
| 2005/0240083 A1 | | 10/2005 | Orban, III | |
| 2006/0074484 A1 | | 4/2006 | Huber | |
| 2007/0083086 A1 | * | 4/2007 | LeVahn | A61B 17/02 600/210 |
| 2007/0112422 A1 | | 5/2007 | Dehdashtian | |
| 2007/0161865 A1 | * | 7/2007 | Fakhrai | A61B 17/0206 600/231 |
| 2007/0299315 A1 | * | 12/2007 | Geller | A61B 17/0206 600/217 |
| 2013/0053863 A1 | * | 2/2013 | Juravic | A61B 17/0206 606/119 |
| 2013/0096387 A1 | * | 4/2013 | DeRidder | A61B 17/0206 600/214 |
| 2015/0209022 A1 | * | 7/2015 | Ruppert | A61B 17/0206 600/219 |
| 2016/0166263 A1 | * | 6/2016 | Sauer | A61B 17/0206 606/79 |
| 2017/0095242 A1 | * | 4/2017 | Milbocker | A61B 17/02 |
| 2017/0172555 A1 | * | 6/2017 | Shimizu | A61B 1/06 |
| 2017/0311940 A1 | * | 11/2017 | Daavettila | A61B 17/0206 |

FOREIGN PATENT DOCUMENTS

| | | | | |
|---|---|---|---|---|
| WO | 9901696 A1 | | 1/1999 | |
| WO | WO-2016164696 A1 | * | 10/2016 | A61B 17/0206 |

OTHER PUBLICATIONS

H. Dave et al., "A Self Retaining Atrial Spreader for Minimally Invasive and Robotically-Assisted Intracardiac Operations"; Cardiothoracic Technique and Technologies IX, Abstract 144, p. 208, The 9th Annual CTI Meeting (Mar. 19, 2003).

Landreneau, et al., "Video-Assisted Thoracic Surgery: Basic Technical Concepts and Intercostal Approach Strategies," Ann. Thoracic Surg., 1992; 54:800-7.

Lone Star Medical Products, Inc., The Lone Star Retractor System brochure/catalog, pp. 1-32, Oct. 2015.

Robinson, et al., "Minimally Invasive Coronary Artery BypassGrafting: A New Method Using an AnteriorMediastinotomy," J. Card. Surg., 1995; 10:529-536.

* cited by examiner

--Prior Art--

--Prior Art--

--Prior Art--

--Prior Art--

--Prior Art--

RIB RETRACTOR WITH COMPLIANT RETRACTOR BLADE

CROSS REFERENCE

This application is a continuation of International Patent Application No PCT/US2021/032509, filed May 14, 2021, which claims the benefit of U.S. Patent Application No. 63/026,289, filed May 18, 2020, the entire disclosures all of which are incorporated by reference for all purposes.

BACKGROUND

Large forces are needed to spread ribs. The forces necessary to separate human ribs are roughly equal to the weight of the person. For example, forces of two hundred pounds (200 lbs) or greater may be necessary. Because of these large forces, employing a rib retractor for thoracic operations can result in broken bones, crushed nerves, wrenched joints, and torn ligaments. These side effects are often treated as acceptable risks of the operations. However, these side effects may require long-term post-operation treatment of the patient. In particular, severe pain may require long-term treatment with strong painkilling drugs. Such treatments are expensive and risk drug addiction. Accordingly, what is needed is a rib retractor that minimizes tissue injury, patient discomfort, and the need for pain management treatment.

SUMMARY

There are provided rib retractors with compliant retractor blades, substantially as shown in and/or described in connection with at least one of the figures, and as set forth more completely in the claims.

DETAILED DESCRIPTION

Figure 1:
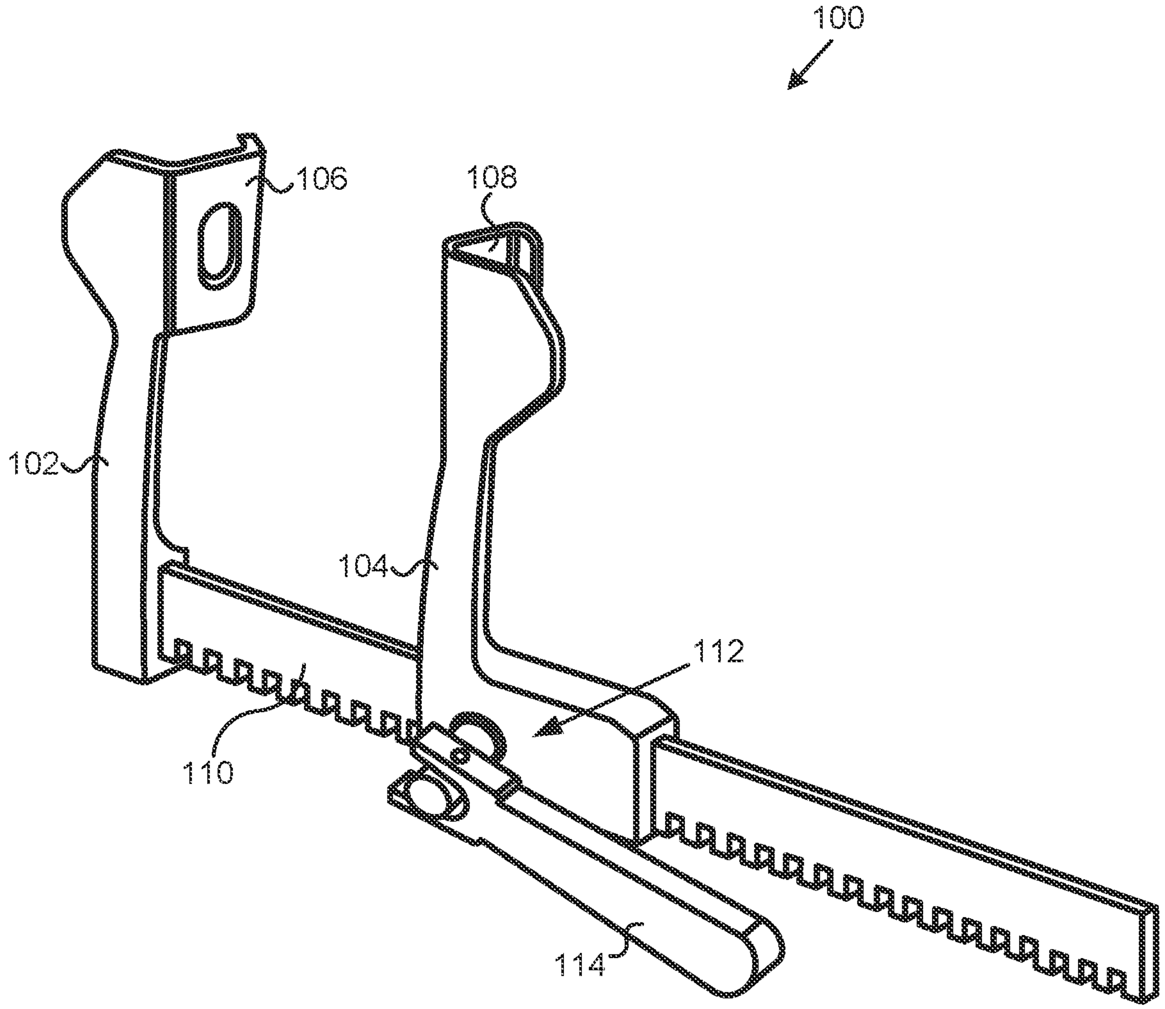
FIG. 1 shows a perspective view of a retractor.

The following description contains specific information pertaining to implementations in the present disclosure. One skilled in the art will recognize that the present disclosure may be implemented in a manner different from that specifically discussed herein. The drawings in the present application and their accompanying detailed description are directed to merely exemplary implementations. Unless noted otherwise, like or corresponding elements among the figures may be indicated by like or corresponding reference numerals. Moreover, the drawings and illustrations in the present application are generally not to scale, and are not intended to correspond to actual relative dimensions.

FIG. 1 shows a perspective view of a retractor. Retractor 100 is known in the art as a Finochietto retractor. Retractor 100 includes arms 102 and 104, blades 106 and 108, rack 110, rack and pinion drive 112, and handle 114. Retractor 100 is a mechanical device utilizing two opposed arms 102 and 104. Arms 102 and 104 are attached to respective blades 106 and 108. One arm 102 is fixedly attached to rack 110. The other arm 104 is moveably attached to rack 110, with motion being driven by rack-and-pinion drive 112. When handle 114 is manually rotated, rack-and-pinion drive 112 applies a retraction force to mechanically retract arm 102 and blade 108 away from opposite arm 104 and blade 106.

In operation, as described further below, blades 106 and 108 are inserted into an incision. In response to the retraction force, blades 106 and 108 engage and impart the retraction force on tissues on either side of the incision, thereby retracting the tissues and opening the incision. When the tissues to be retracted include ribs or other bones, large forces need to be imparted. In order to withstand these large forces, retractor 100 is typically formed of metal, such as stainless steel, or of other non-compliant materials. As used herein, "non-compliant material" refers to any material having flexural stiffness significantly greater than bone, such that it will experience little to no deformation in response to retraction forces large enough to bend or break bone.

Figure 2A:
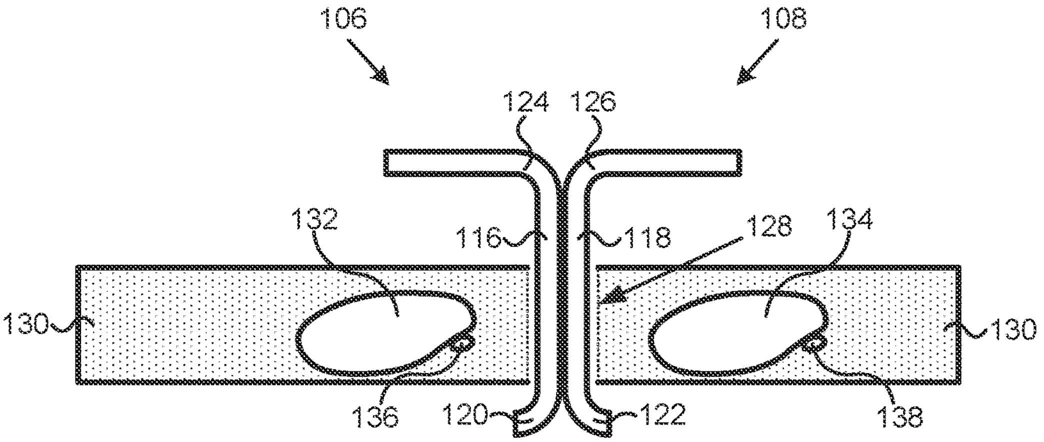
FIG. 2A shows a side cross-sectional view of the retractor of FIG. 1 in use.

FIG. 2A shows a side cross-sectional view of retractor 100 of FIG. 1 in use. The cross-sectional view in FIG. 2A includes blades 106 and 108 having respective descender portions 116 and 118, respective first hook portions 120 and 122, and respective second hook portions 124 and 126, incision 128, tissue 130, ribs 132 and 134, and neurovascular bundles 136 and 138. Blades 106 and 108 in FIG. 2A generally correspond to blades 106 and 108 in FIG. 1. Rib 132 may be a cranial rib closer to a patient's head. Rib 134 may be a caudal rib closer to a patient's tail. Although tissue 130 is illustrated as a single layer in FIG. 2A, tissue 130 can include various tissue layers, such as outer skin, intercostal muscles, and other connective tissue. Neurovascular bundles 136 and 138 are delicate bundles of nerves and arteries laying just inside the caudal edge of ribs 132 and 134. Neurovascular bundles 136 and 138 include the particularly delicate intercostal nerves, as described below.

As shown in FIG. 2A, blades 106 and 108 are inserted into incision 128 in tissue 130 between ribs 132 and 134. First hook portions 120 and 122 reach below tissue 130 and ribs 132 and 134, for example, into a thoracic cavity. Descender portions 116 and 118 are connected to respective first hook portions 120 and 122. Descender portions 116 and 118 span the thickness of ribs 132 and 134 and tissue 130. Second hook portions 124 and 126 are connected to respective descender portions 116 and 118, and reach above tissue 130 and ribs 132 and 134. Second hook portions 124 and 126 extend farther away from respective descender portions 116 and 118 than respective first hook portions 120 and 122, such that blades 106 and 108 may rest atop tissue 130 when the retractor is not being held. It is noted that the illustrated dimensions are generally not to scale and may be exaggerated for the purpose of illustration. Blades 106 and 108, and portions thereof, may have any other relative dimensions than those shown in FIG. 2A.

Figure 2B:
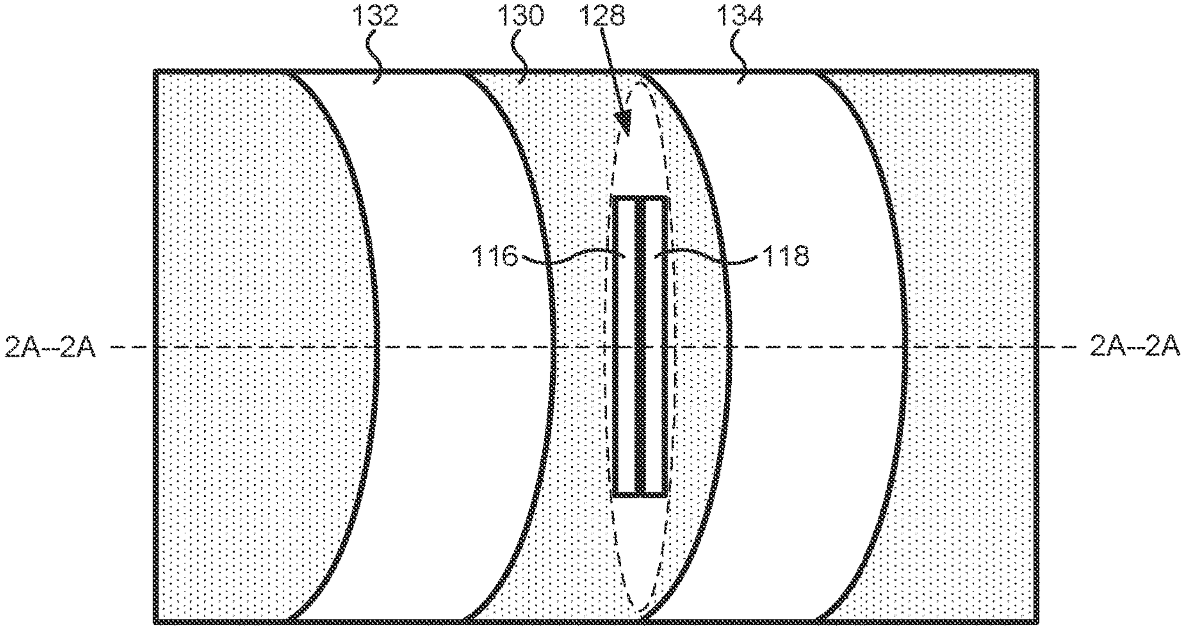
FIG. 2B shows a top cross-sectional view corresponding to FIG. 2A.

FIG. 2B shows a top cross-sectional view corresponding to FIG. 2A. FIG. 2A shows a cross sectional view along line "2A-" in FIG. 2B. As shown in FIG. 2B, when blades 106 and 108 (shown in FIG. 2A) are inserted into incision 128 in tissue 130 between ribs 132 and 134, descender portions 116 and 118 lie along a plane between ribs 132 and 134. Descender portions 116 and 118 are substantially linear along their lengths. Rib 132 is substantially convex along the length of its caudal edge that faces blade 106. Rib 134 is substantially concave along the length of its cranial edge that faces blade 108. Although incision 128 is shown as a slit roughly centered between ribs 132 and 134, in various implementations, incision 128 may have various dimensions and/or positioning between ribs 132 and 134.

Figure 3A:
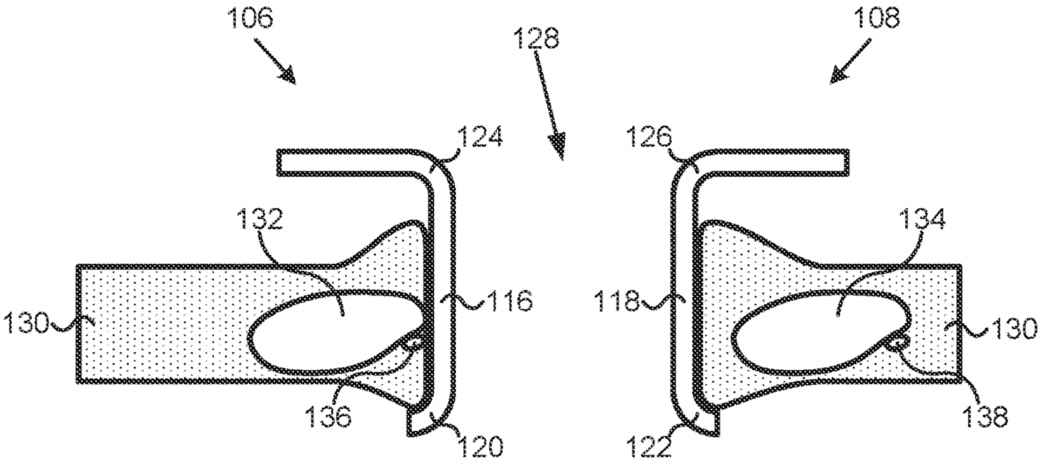
FIG. 3A shows a side cross-sectional view of the retractor of FIG. 1 in use.

FIG. 3A shows a side cross-sectional view of retractor 100 of FIG. 1 in use. As shown in FIG. 3A, a retraction force is applied to blades 106 and 108, for example, by handle 114 and rack-and-pinion drive 112 (shown in FIG. 1). In response to the retraction force, blades 106 and 108 mechanically retract away from each other, opening incision 128. Blades 106 and 108 engage respective ribs 132 and 134, imparting the retraction force on ribs 132 and 134, and pushing the ribs 132 and 134 apart. Portions of tissue 130 between blade 106 and rib 132 are compressed. Similarly, portions of tissue 130 between blade 108 and rib 134 are compressed. First hook portions 120 and 122 and second hook portions 124 and 126 prevent these portions of tissue 130 from slipping into the opening created by blades 106 and 108.

Figure 3B:
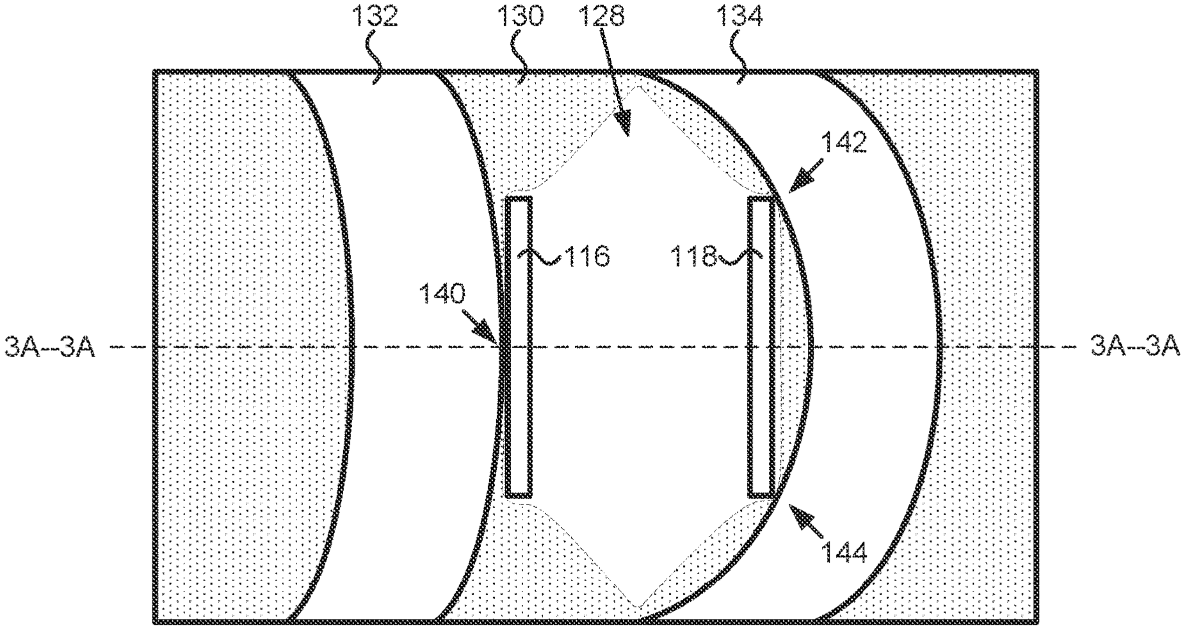
FIG. 3B shows a top cross-sectional view corresponding to FIG. 3A.

FIG. 3B shows a top cross-sectional view corresponding to FIG. 3A. FIG. 3A shows a cross sectional view along line "3A-" in FIG. 3B. As shown in FIG. 3B, when blades 106 and 108 (shown in FIG. 3A) retract, descender portions 116 and 118 engage and retract ribs 132 and 134, compress portions of tissue 130, and open incision 128, as described above. Ribs 132 and 134 bend as they retract. However, because blades 106 and 108 are formed of non-compliant material, such as stainless steel, descender portions 116 and 118 do not bend and remain substantially linear along their lengths. As a result, descender portion 116 engages the convex edge of rib 132 around a single high pressure point 140, and descender portion 118 engages the concave edge of rib 134 around a pair of high-pressure points 142 and 144.

Due to the large retraction force needed to retract ribs 132 and 134, compressed portions of tissue 130 between blade 106 and rib 132, and between blade 108 and rib 134, can be damaged. These portions of tissue 130 remain compressed for the duration of a thoracic operation, increasing the severity of the damage compared to a scenario where ribs 132 and 134 are quickly returned to their initial positions. The high pressure from compressed portions of tissue 130 also damages neurovascular bundle 136 (shown in FIG. 3A). Damage to the intercostal nerve in neurovascular bundle 136 is a primary cause of severe post-operation pain. At high pressure points 140, 142, and 144 in particular, tissue 130 is crushed, and damage to the intercostal nerve in neurovascular bundle 136 is the most severe. Additionally, ribs 132 and 134 are particularly likely to crack around high-pressure points 140, 142, and 144, causing further pain.

Figure 4:
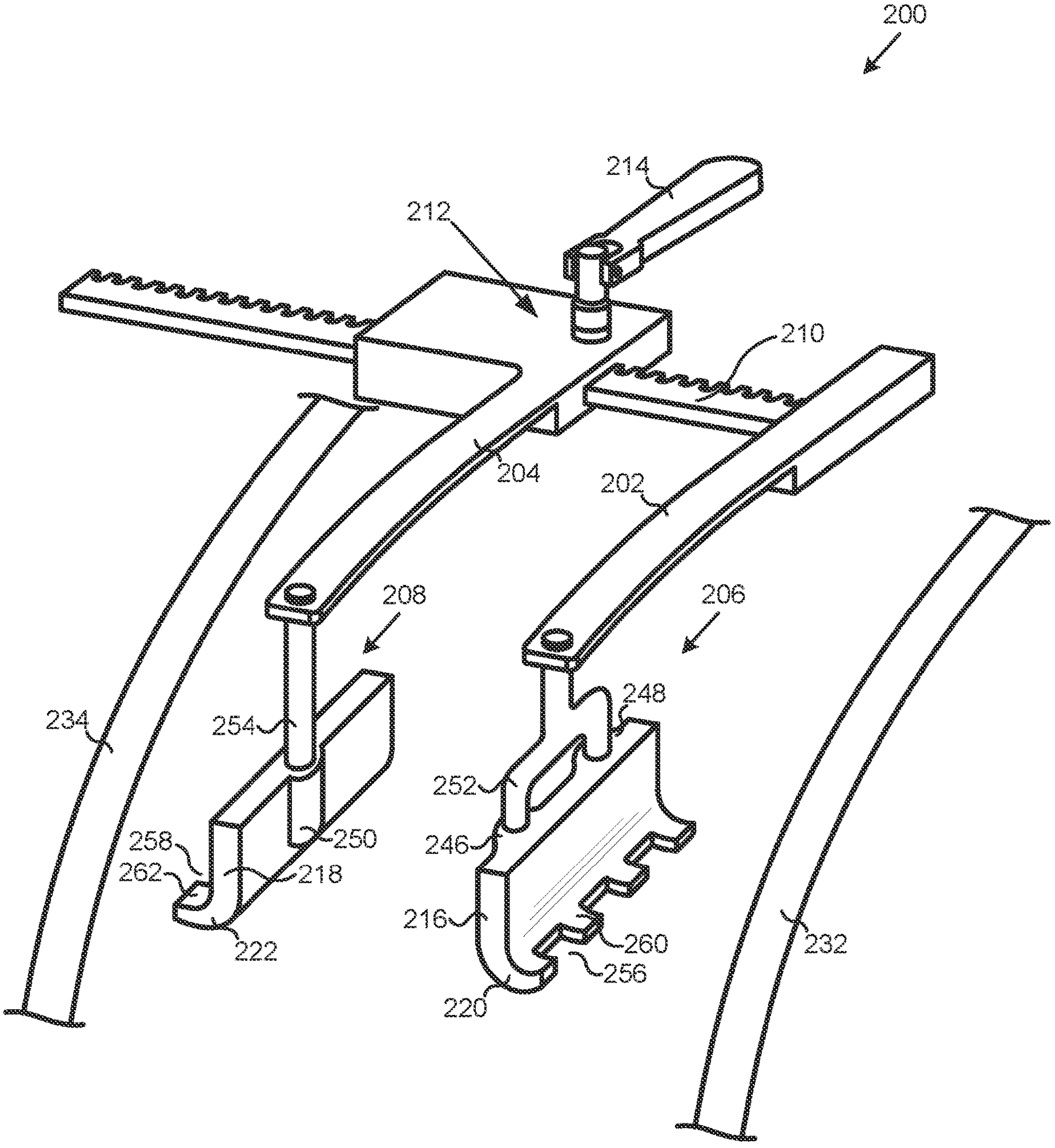
FIG. 4 shows a perspective view of an exemplary retractor, according to one implementation of the present application.

FIG. 4 shows a perspective view of an exemplary retractor, according to one implementation of the present application. Retractor 200 includes arms 202 and 204, blades 206 and 208, rack 210, rack and pinion drive 212, and handle 214. Blade 206 includes descender portion 216, hook portion 220, humps 246 and 248, and pivot connector 252. Blade 208 includes descender portion 218, hook portion 222, hump 250, and pivot connector 254. Also shown in FIG. 4 are ribs 232 and 234.

Arms 202 and 204, rack 210, rack and pinion drive 212, and handle 214 in FIG. 4 generally correspond to arms 102 and 104, rack 110, rack and pinion drive 112, and handle 114 in FIG. 1. For example, arm 202 is fixedly attached to rack 210, arm 204 is moveably attached to rack 210, and when handle 214 is manually rotated, rack-and-pinion drive 212 applies a retraction force to mechanically retract arm 202 and blade 208 away from opposite arm 204 and blade 206. In various implementations, arm 202 may be moveable while arm 204 is fixed, or both arms 202 and 204 may be moveable, with respect to rack 210. In one implementation, blades 206 and 208 can be lowered into an incision between ribs 232 and 234 while the remaining body of retractor 200 rests atop adjacent skin. For example, arms 202 and 204 can be angled, or can include reconfigurable angling joints, or can include any other mechanisms known in the art.

Blades 206 and 208 are pivotably attached to respective arms 202 and 204 by respective pivot connectors 252 and 254. Pivot connectors 252 and 254 transfer the retraction force from respective arms 202 and 204 to respective blades 206 and 208. In particular, blades 206 and 208 receive the retraction force from their respective back surfaces. Pivot connectors 252 and 254 also enable blades 206 and 208 to pivot with respect to arms 202 and 204. Thus, blades 206 and 208 may pivot to engage ribs 232 and 234 even where a user does not hold arms 202 and 204 properly aligned with ribs 232 and 234. As described below, pivoting causes blades 206 and 208 to deform more evenly along their lengths and reduces pressure on tissues.

In the present implementation, pivot connectors 252 and 254 are substantially tubular. Pivot connectors 252 and 254 attach through the bottoms of respective arms 202 and 204, and are secured on the tops of arms 202 and 204. In other implementations, pivot connectors 252 and 254 may utilize other shapes and pivoting attachment mechanisms know in the art. For example, pivot connectors 252 and 254 may utilize annular clips to attach to buckles in arms 202 and 204. As another example, pivot connectors 252 and 254 and arms 202 and 204 may have holes that can be aligned and secured with a pin or screw. As another example, pivot connectors 252 and 254 may pivotably attach to arms 202 and 204 using a mechanical lock or spring lock with and button release. In the present implementation, pivot connectors 252 and 254 are integrally formed of the same material as blades 206 and 208. In another implementation, pivot connectors 252 and 254 may be formed separately from and attached to blades 206 and 208.

Notably, pivot connector 252 is forked, while pivot connector 254 is not. Also, blades 206 and 208 are asymmetrical. Blade 206 includes two humps 246 and 248, while blade 208 includes one hump 250. These configurations aid blade 206 in engaging the convex edge of rib 232, and aid blade 208 in engaging the concave edge of rib 234. Humps 246 and 248 receive pivot connector 252 and receive the retraction force at outside portions of blade 206. Blade 206 can thus conform to the convex edge of rib 232, as described below. Hump 250 receives pivot connector 254 and receives the retraction force at a central portion of blade 208. Blade 208 can thus conform to the concave edge of rib 234, as described below. It is noted that humps 246, 248 and 250 may have shapes and dimensions other than those shown in FIG. 4, while still receiving the retraction force from the back surface at outside or central portions of blades 206 and 208.

As shown in FIG. 4, blades 206 and 208 include respective descender portions 216 and 218 and respective hook portions 220 and 222. Hook portions 220 and 222 include respective gaps 256 and 258 and respective teeth 260 and 262. Additional details regarding blades 206 and 208 are described below.

Figure 5:
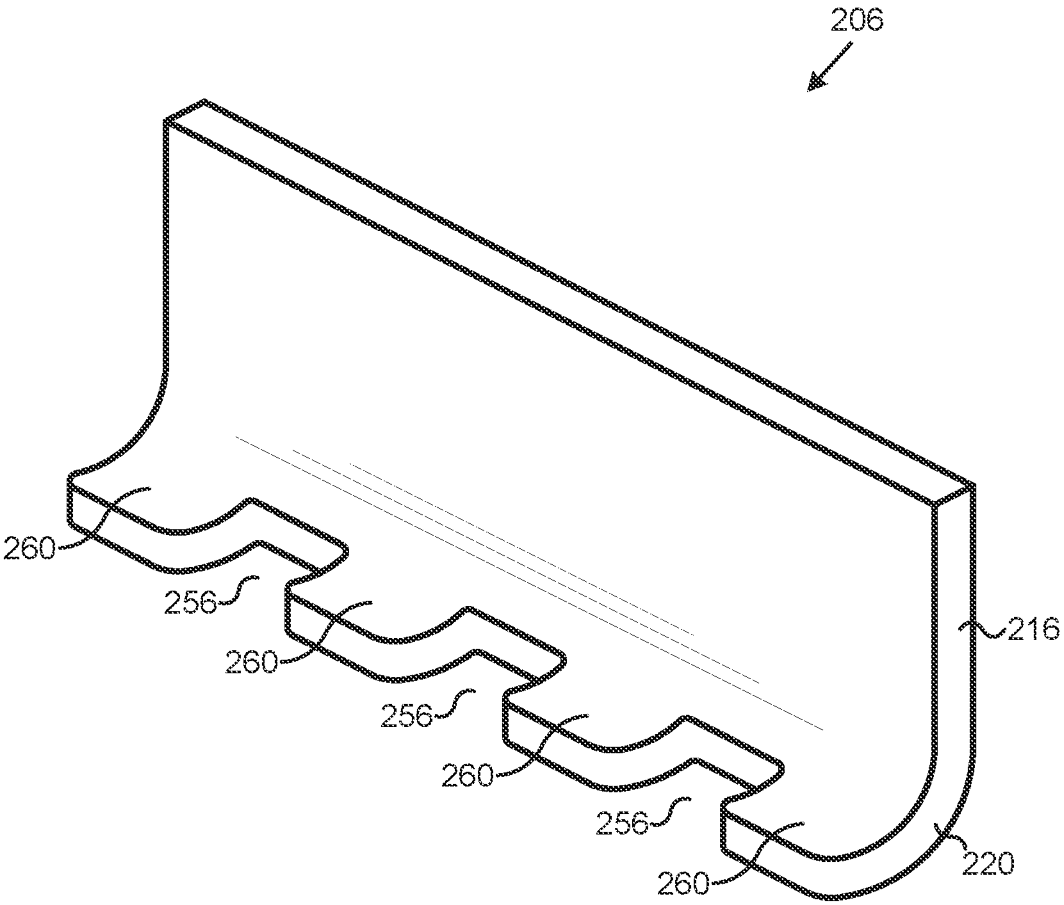
FIG. 5 shows a perspective view of an exemplary retractor blade, according to one implementation of the present application.

FIG. 5 shows a perspective view of an exemplary retractor blade, according to one implementation of the present application. Blade 206 in FIG. 5 may generally correspond to blade 206 in FIG. 4. Blade 208 in FIG. 4 may have any implementations or advantages described with respect to blade 206 in FIG. 5. Blade 206 may include additional features not shown in FIG. 5, such as a pivot connector or hump.

Blade 206 includes descender portion 216 and hook portions 220. In the present implementation, descender portion 216 is substantially rectangular. The height of descender portions 216 may be configured to span the thickness of a rib, such as rib 232 in FIG. 4, and its underlying and overlying tissue, such as tissue 130 in FIG. 1. For example, descender portion 216 may be approximately two centimeters to approximately four centimeters (2 cm-4 cm). In operation, descender portion 216 engages a rib in response to the retraction force applied to the retractor blade, as described above.

Hook portion 220 is a portion of blade 206 that is angled with respect to descender portion 216. Due to this angle, hook portion 220 forms a channel with descender portion 216 on the front surface of blade 206. This channel secures the rib against the descender portion 216, offering resistance to vertical slip. In operation, hook portion 220 reaches below the rib and its underlying tissue, for example, into a thoracic cavity. In the present implementation, hook portion 220 is approximately a ninety-degree arc. Thus, the channel created by hook portion 220 and descender portion 216 has a "J" shape. In other implementations, hook portion 220 may have any angle, dimensions, and curvature. For example, the channel created by hook portion 220 and descender portion 216 may have an "L" shape or a fishhook shape. Generally speaking, when the angle of hook portion 220 is farther from flush with descender portion 216, the rib will be more secure, but the rib and tissue will experience more pressure. Additionally, smaller dimensions of hook portion 220 may allow easier insertion of blade 206 into an incision, but the rib may be less secure.

As shown in FIG. 5, descender portion 216 and hook portion 220 of blade 206 are integrally formed. Pivot connector 252 and humps 246 and 248 (shown in FIG. 4) of blade 206 may also be integrally formed with descender portion 216 and hook portion 220. Unlike blade 106 (shown in FIG. 1), blade 206 is formed of a compliant material. For example, blade 206 may be formed of polypropylene or polyethylene, rather than steel. As another example, blade 206 may be formed of a compliant ceramic material. As used herein, "compliant material" refers to any material having flexural stiffness that is not significantly greater than bone, e.g. polypropylene or polyethylene, such that the material can deform in response to retraction forces large enough to bend or break bone.

As also shown in FIG. 5, hook portion 220 includes gaps 256 separating teeth 260 along the length of hook portion 220. Gaps 256 represent breaks in the continuity of hook portion 220. In the present implementation, hook portion 220 includes three gaps 256 separating four teeth 260. Gaps 256 and teeth 260 have a rounded rectangular shape. Gaps 256 extend approximately halfway up from the end of hook portion 220 toward descender portion 216. Gaps 256 cut through the thickness of hook portion 220, extending from the front surface to the back surface of blade 206. In various implementations, hook portion 220 can include more or fewer gaps 256 and/or teeth 260. The number of gaps 256 may be chosen based on the length of hook portion 220, for example, such that blade 206 achieves a certain frequency of gaps 256. In various implementations, gaps 256 and teeth 260 may have other shapes, such as, for example, right rectangles, half circles, ovals, triangles, or inverted versions of such shapes. In one implementation, gaps 256 are portions of hook portion 220 thinned from the front and/or back surface of blade 206 relative to teeth 260.

Gaps 256 generally influence the rate of deformation of blade 206, based on their numbers and dimensions. For example, gaps 256 that extend deeper from the end of hook portion 220 toward descender portion 216 may cause blade 206 to deform in response to a retraction force of approximately one hundred pounds, while gaps 256 that extend shallower from the end of hook portion 220 toward descender portion 216 may cause blade 206 to deform in response to a retraction force of approximately two hundred pounds. Likewise, a greater number of gaps generally causes blade 206 to deform in response to a lesser retraction force. As described below, because blade 206 includes gaps 256 in hook portion 220 and is formed of compliant material, descender portion 216 conforms to a rib in response to retraction force.

Figure 6A:
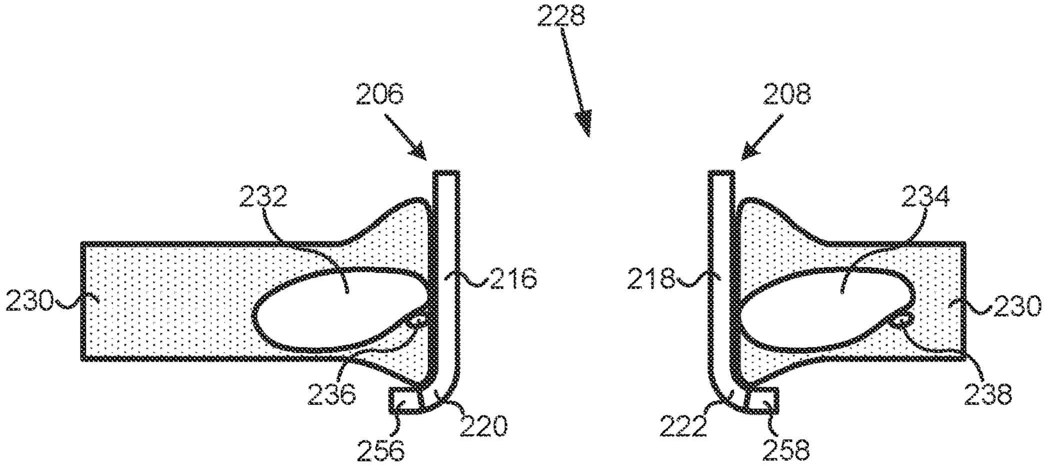
FIG. 6A shows a side cross-sectional view of the retractor of FIG. 4 in use.

FIG. 6A shows a side cross-sectional view of retractor 200 of FIG. 4 in use. The cross-sectional view in FIG. 6A includes blades 206 and 208 having respective descender portions 216 and 218, respective hook portions 220 and 222 including respective gaps 256 and 258, incision 228, tissue 230, ribs 232 and 234, and neurovascular bundles 236 and 238. Blades 206 and 208 and ribs 232 and 234 in FIG. 6A generally correspond to blades 206 and 208 and ribs 232 and 234 in FIG. 4. Blades 206 and 208 may include additional features not shown in FIG. 6A, such as a pivot connector or hump. Tissue 230 and neurovascular bundles 236 and 238 in FIG. 6A generally correspond to tissue 130 and neurovascular bundles 136 and 138 in FIG. 2A.

As shown in FIG. 6A, a retraction force is applied to blades 206 and 208, for example, by handle 214 and rack-and-pinion drive 212 (shown in FIG. 4). In response to the retraction force, blades 206 and 208 mechanically retract away from each other, opening incision 228. Descender portions 216 and 218 engage respective ribs 232 and 234 and push ribs 232 and 234 apart. Hook portions 220 and 222 secure ribs 232 and 234 against respective descender portions 216 and 218. Referring back to FIG. 3A, descender portion 118 in the cross-sectional view of FIG. 3A is separated from rib 134 by a significant volume of intervening tissue 130. In contrast, descender portion 218 in the cross-sectional view of FIG. 6A engages rib 234 with less intervening tissue 230. As described below, this is because gaps 258 in hook portion 222 and compliant material cause the entire length of blade 208 in descender portion 218 to conform to rib 234. Notably, the height of blade 208 in descender portion 218 does not conform, for example, over the top of rib 234.

Figure 6B:
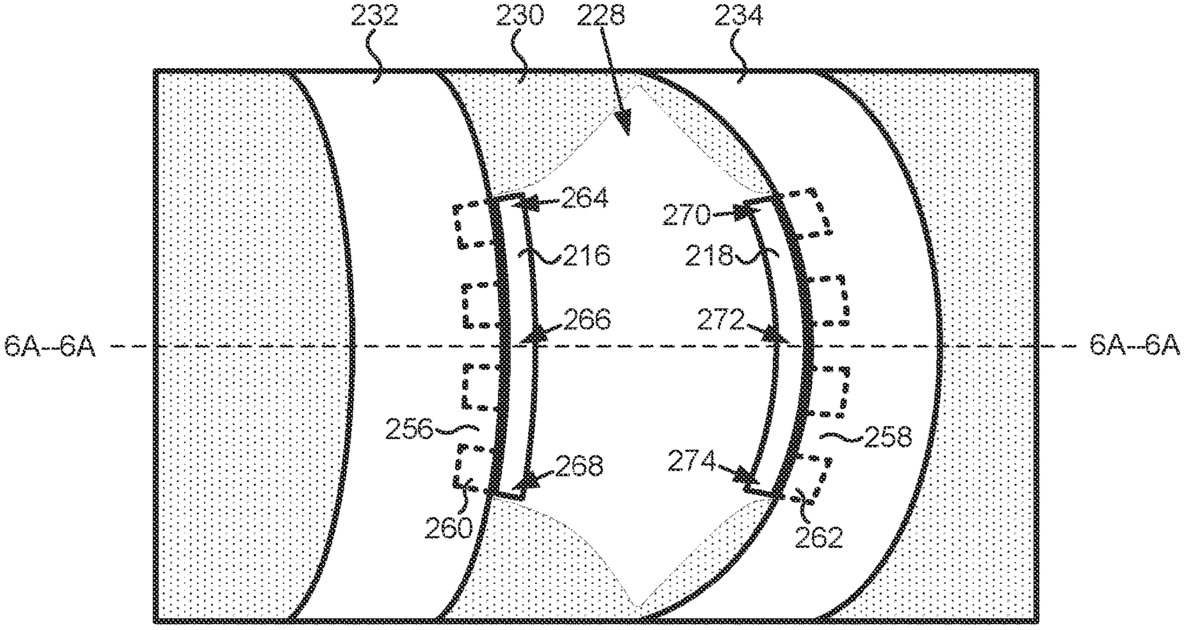
FIG. 6B shows a top cross-sectional view corresponding to FIG. 6A.

FIG. 6B shows a top cross-sectional view corresponding to FIG. 6A. FIG. 6A shows a cross sectional view along line "6A-" in FIG. 6B. As shown in FIG. 6B, when blades 206 and 208 (shown in FIG. 6A) retract, descender portions 216 and 218 engage and retract ribs 232 and 234, compress portions of tissue 230, and open incision 228, as described above. Ribs 232 and 234 bend as they retract. Referring back to FIG. 3B, descender portions 116 and 118 do not bend, remain substantially linear along their lengths, and engage ribs 132 and 134 at high pressure points 140, 142, and 144. In contrast, in the cross-sectional view of FIG. 6B, the entire length of blade 206 in descender portion 216 conforms to rib 232, and the entire length of blade 208 in descender portion 218 conforms to rib 234. Notably, in a resting state, descender portions 216 and 218 may be substantially linear along their lengths. However, because blades 206 and 208 include gaps 256 and 258 in hook portions 220 and 222 and are formed of compliant material, blades 206 and 208 will deform in response to a retraction force upon engaging ribs 232 and 234. As a result, the entire lengths of descender portions 216 and 218 conform to respective ribs 232 and 234 they retract. Gaps 256 and 258 and teeth 260 and 262 may also contract or expand. Dotted outlines in FIG. 6B illustrate gaps 256 and 258 and teeth 260 and 262 as seen through ribs 232 and 234.

Because the entire lengths of blades 206 and 208 in descender portions 216 and 218 conform to respective ribs 232 and 234, the retraction force is distributed across larger areas of tissue 230 and ribs 233 and 234, rather than at high pressure points 140, 142, and 144 (shown in FIG. 3B). Ribs 232 and 234 are less likely to crack, less overall damage occurs to compressed portions of tissue 230, tissue 230 is not crushed at a particular high-pressure point, and damage to the intercostal nerve in neurovascular bundle 236 (shown in FIG. 6A) is avoided. As described above, the intercostal nerve in neurovascular bundle 236 is a primary cause of severe post-operation pain. In one implementation, only blade 206 that engages rib 232 near neurovascular bundle 236 is formed of compliant material, while blade 208 that engages rib 234 opposite neurovascular bundle 238 is formed of non-compliant material, similar to blade 108 in FIG. 1.

In the present implementation, blades 206 and 208 may exhibit temporary elastic (i.e., reversible) deformation. In another implementation, blades 206 and 208 may exhibit permanent plastic (i.e., irreversible) deformation. In either implementation, blades 206 and 208 may be reusable. For example, where blades 206 and 208 exhibit permanent plastic (i.e., irreversible) deformation, a molding device may be used to deform them back to their initial shape.

The lengths of blades 206 and 208 in descender portions 216 and 218 may deform more than the height of blades 206 and 208 in descender portions 216 and 218. For example, due to gaps 256 and teeth 260, the entire length of blade 206 in descender portion 216 may conform along the caudal edge of rib 232 (as shown in FIG. 6B), while the height of blade 206 in descender portion 216 does not conform, for example, over the top edge of rib 234 (as shown in FIG. 6A). As a result, the blade may be less likely to slip out of incision 228, and the retraction force may be distributed across a larger area along the length of rib 234, rather than a smaller circumferential area. In one implementation, blades 206 and 208 may employ spines to influence deformation in descender portions 216 and 218, as described further below.

Pivot connectors 252 and 254 also enable blades 206 and 208 to pivot with respect to arms 202 and 204. Thus, blades 206 and 208 may pivot to engage ribs 232 and 234 even where a user does not hold arms 202 and 204 properly aligned with ribs 232 and 234. As described below, pivoting causes blades 206 and 208 to deform more evenly along their lengths and reduces pressure on tissues.

Advantageously, because blades 206 and 208 are capable of pivoting, as described above, blades 206 and 208 can avoid creating high pressure regions on tissue 230, which may otherwise occur where a user does not properly align retractor 200 (shown in FIG. 4). For example, in FIG. 6B blades 206 and 208 are aligned roughly parallel with ribs 232 and 234. However, in another scenario, blades 206 and 208 may be inserted into incision 228 thirty degrees clockwise from their positions in FIG. 6B due to improper alignment of retractor 200. In this scenario, if blades 206 and 208 could not pivot, as blades 206 and 208 retract, blade 206 may initially engage rib 232 at a point on the outer portion 268 of blade 206, rather than at a point on the central portion 266 of blade 206. Meanwhile, blade 208 may initially engage rib 234 at a point on the outer portion 270 of blade 208, rather than at points on both outer portions 270 and 274 of blade 208. As blades 206 and 208 continue to retract, the outer portion 264 of blade 206 will need to deform more in order for the entire length of blade 206 to conform to rib 232. High pressures will be exerted on tissue 230 near outer portion 268 and central portion 266 compared to outer portion 264. Meanwhile, the outer portion 274 of blade 208 will need to deform more in order for its entire length to conform to rib 234. High pressures will be exerted on tissue 230 near outer portion 270 and central portion 272 compared to outer portion 274. However, because blades 206 and 208 are capable of pivoting, as blades 206 and 208 retract, blade 206 may pivot to initially engage ribs 232 at central portion 266, and blade 208 may pivot to engage rib 234 at both outer portions 270 and 274, despite misalignment. As blades 206 and 208 continue to retract, they will deform more evenly along their lengths and reduce pressure on tissue 230.

Figure 7:
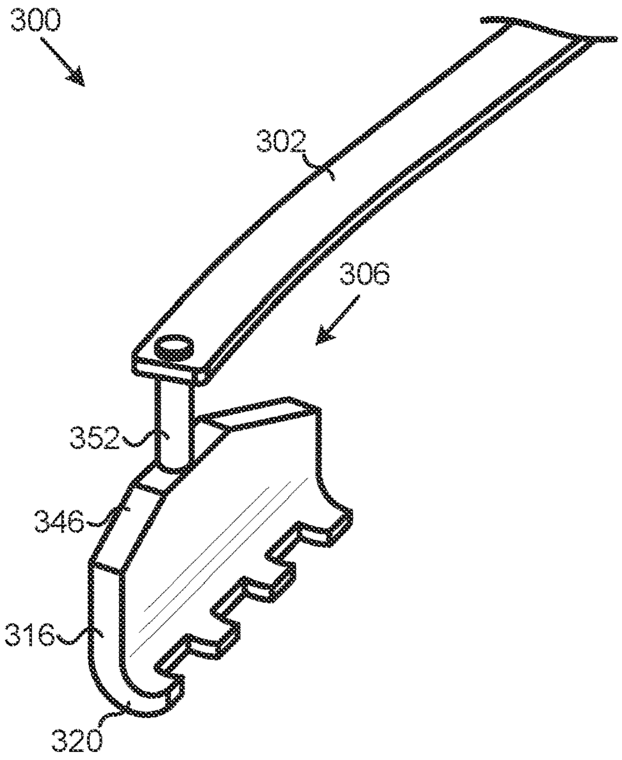
FIG. 7 shows a perspective view of a portion of an exemplary retractor, according to one implementation of the present application.

FIG. 7 shows a perspective view of a portion of an exemplary retractor, according to one implementation of the present application. The portion of retractor 300 in FIG. 7 shows arm 302 and blade 306. Blade 306 includes descender portion 316, hook portion 320, hump 346, and pivot connector 352. Arm 302, descender portion 316, and hook portion 320 in FIG. 7 generally correspond to arm 202, descender portion 216, and hook portion 220 in FIG. 4. Retractor 300 in FIG. 7 represents an alternate implementation to retractor 200 in FIG. 4, where blade 306 receives the retraction force from its top surface opposite hook portion 320. Pivot connector 352 transfers the retraction force from arm 302 to respective blade 306. Hump 346 receives pivot connector 352 and receives the retraction force from the top surface of blade 306. In the present implementation, hump 346 has a trapezoidal pyramid shape. Hump 346 distributes the retraction force along the length of descender portion 316. Blade 306 can thus conform to either concave or convex edges of ribs, and is suitable for use in a retractor with symmetrical blades. For example, both blades 206 and 208 in FIG. 4 can be replaced with blade 306 in FIG. 7. It is noted that hump 346 may have shapes and dimensions other than those shown in FIG. 7, while still receiving the retraction force from the top surface of blade 306.

Figure 8:
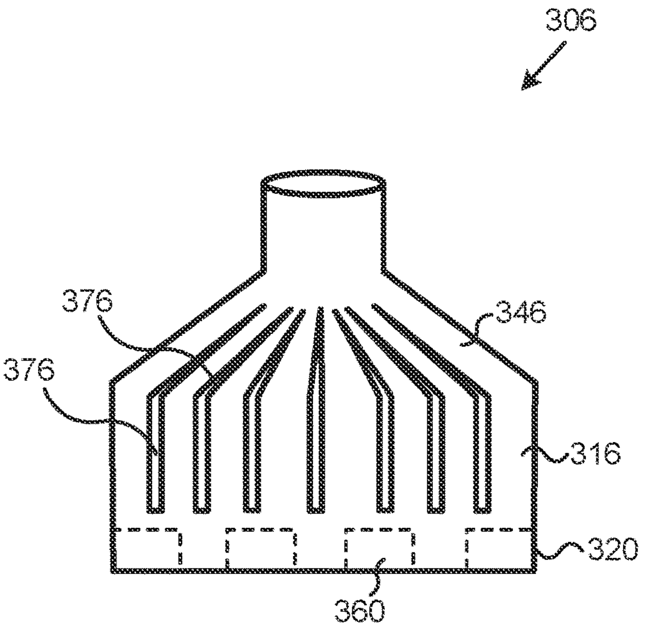
FIG. 8 shows a back view of an exemplary retractor blade, according to one implementation of the present application.

FIG. 8 shows a back view of an exemplary retractor blade, according to one implementation of the present application. Blade 306 in FIG. 8 generally corresponds to blade 306 in FIG. 7. Dotted outlines in FIG. 8 illustrate teeth 360 of hook portion 320 as seen through blade 306. As shown in FIG. 8, blade 306 employs spines 376 along its back surface. Spines 376 are raised members that run along the back surface of blade 306, for example, along descender portion 316 and/or hump 346. Spines 376 may be integrally formed with descender portion 316 and/or hump 346 of a compliant material. Spines 376 increase the flexural stiffness along the height of blade 306 relative to the flexural stiffness along the length of blade 306, particularly in descender portion 316. As a result, the length of blades 306 in descender portion 316 may conform to a rib, such as rib 232 in FIG. 6A, while the height of blade 306 in descender portion 316 does not, as described above.

Figure 9:
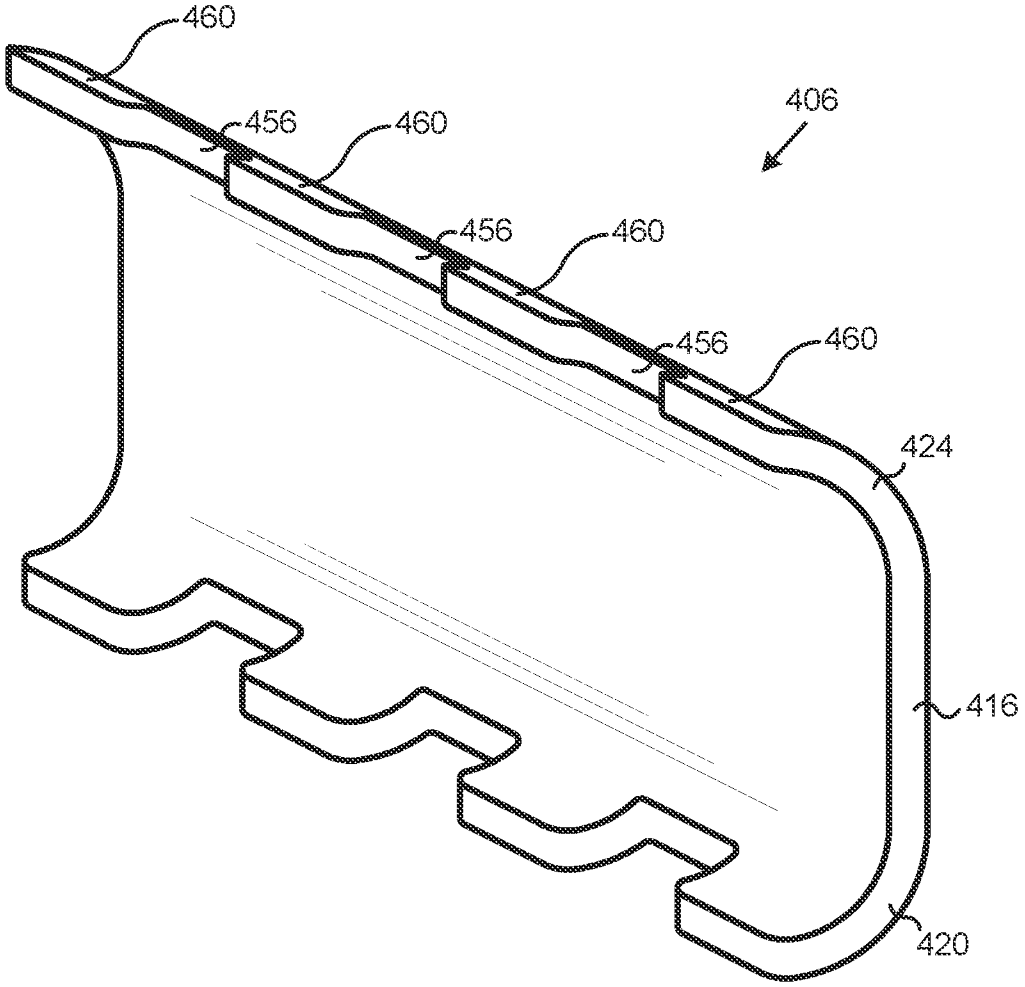
FIG. 9 shows a perspective view of an exemplary retractor blade, according to one implementation of the present application.

FIG. 9 shows a perspective view of an exemplary retractor blade, according to one implementation of the present application. Blade 406 in FIG. 9 represents an alternate implementation to blade 206 in FIG. 5, where blade 406 includes a second hook portion 424 opposite first hook portion 420. Second hook portion 424 is integrally formed of the same compliant material as descender portion 416 and first hook portion 420. Second hook portion 424 forms a channel with descender portion 416 and first hook portion 420 on the front surface of blade 406. This channel further secures the rib against the descender portion 416, offering resistance to vertical slip. The channel has a bracket shape. In other implementations, the channel may have a "C" shape. In operation, second hook portion 424 may rest atop tissue 230 (shown in FIG. 6A). Second hook portion 424 also includes gaps 456 separating teeth 460 along the length of second hook portion 424. Gaps 456 and teeth 460 further influence the rate of deformation of blade 406, and may have any implementations or advantages described above. In the present implementation, gaps 456 and teeth 460 in second hook portion 424 are symmetrical to those in first hook portion 420. In other implementations, second hook portion 424 and first hook portion 420 may be asymmetrical.

Thus, the present application discloses various implementations of rib retractors with compliant retractor blades. From the above description it is manifest that various techniques can be used for implementing the concepts described in the present application without departing from the scope of those concepts. Moreover, while the concepts have been described with specific reference to certain implementations, a person of ordinary skill in the art would recognize that changes can be made in form and detail without departing from the scope of those concepts. As such, the described implementations are to be considered in all respects as illustrative and not restrictive. It should also be understood that the present application is not limited to the particular implementations described herein, but many rearrangements, modifications, and substitutions are possible without departing from the scope of the present disclosure.

What is claimed is:

1. A retractor blade comprising:

a descender portion configured to engage a rib in response to a retraction force applied to the retractor blade;

a first hook portion forming a channel with the descender portion, the channel configured to secure the rib against the descender portion;

a first hump and a second hump each protruding from a back surface of the retractor blade opposite a front surface of the retractor blade, the front surface including the channel;

wherein the descender portion and the first hook portion are integrally formed of a compliant material;

wherein the first hook portion includes at least one gap separating a first plurality of teeth;

wherein the at least one gap of the first hook portion and the compliant material together are configured to cause substantially an entire length of the retractor blade in the descender portion to conform to the rib in response to the retraction force; and wherein the first hump is configured to receive a first fork of a forked pivot connector to a retractor arm, and wherein the second hump is configured to receive a second fork of the forked pivot connector.

2. The retractor blade of claim 1, wherein the at least one gap has a rounded rectangular shape.

3. The retractor blade of claim 1, wherein the channel has an "L" shape or a "J" shape.

4. The retractor blade of claim 1, wherein substantially an entire height of the retractor blade in the descender portion does not conform to the rib in response to the retraction force.

5. A retractor comprising:

means for applying a retraction force;

first and second arms;

at least one of the first and second arms configured to mechanically retract in response to the retraction force;

first and second retractor blades attached respectively to the first and second arms, the first and second retractor blades being asymmetrical;

wherein the first retractor blade is pivotably attached to the first arm;

the first retractor blade comprising:

a first descender portion configured to engage a first rib in response to the retraction force;

a first hook portion forming a first channel with the first descender portion, the first channel configured to secure the first rib against the first descender portion;

at least one hump protruding from a back surface of the retractor blade opposite a front surface of the retractor blade, the front surface including the channel;

wherein the first descender portion and the first hook portion are integrally formed of a compliant material;

wherein the first hook portion includes at least one gap separating a first plurality of teeth;

wherein the at least one gap of the first hook portion and the compliant material together are configured to cause substantially an entire length of the first retractor blade in the first descender portion to conform to the first rib in response to the retraction force; and wherein the at least one hump comprises a first hump and a second hump, and wherein the first hump is configured to receive a first fork of a forked pivot connector to the first arm, and wherein the second hump is configured to receive a second fork of the forked pivot connector.

6. The retractor of claim 5, wherein the second retractor blade is formed of a non-compliant material.

7. The retractor of claim 5, wherein the second retractor blade is pivotably attached to the second arm;

the second retractor blade comprising:

a second descender portion configured to engage a second rib in response to the retraction force;

a second hook portion forming a second channel with the second descender portion, the second channel configured to secure the second rib against the second descender portion;

wherein the second descender portion and the second hook portion are integrally formed of the compliant material;

wherein the second hook portion includes at least one gap separating a second plurality of teeth;

wherein the at least one gap of the second hook portion and the compliant material together are configured to cause substantially an entire length of the second retractor blade in the second descender portion to conform to the second rib in response to the retraction force.

8. The retractor of claim 7, wherein the first retractor blade is configured to compliantly engage a convex portion of the first rib and the second retractor blade is configured to compliantly engage a concave portion of the second rib.

9. The retractor of claim 8, wherein the first retractor blade is configured to receive the retraction force at outside portions, and the second retractor blade is configured to receive the retraction force at a central portion.

10. The retractor of claim 5, wherein the means for applying the retraction force comprises a rack and pinion.

11. The retractor of claim 5, wherein the at least one gap has a rounded rectangular shape.

12. The retractor of claim 5, wherein the first channel has an "L" shape or a "J" shape.

* * * * *